US007339658B2

(12) United States Patent
Beyerlein et al.

(10) Patent No.: US 7,339,658 B2
(45) Date of Patent: Mar. 4, 2008

(54) DEVICE AND METHOD FOR MEASURING SURFACE TOPOGRAPHY AND WAVE ABERRATION OF A LENS SYSTEM, IN PARTICULAR AN EYE

(75) Inventors: Mathias Beyerlein, Erlangen (DE); Johannes Pfund, Nürnberg (DE)

(73) Assignee: Optocraft GmbH, Erlangen (DE)

( * ) Notice: Subject to any disclaimer, the term of this patent is extended or adjusted under 35 U.S.C. 154(b) by 132 days.

(21) Appl. No.: 11/374,510

(22) Filed: Mar. 13, 2006

(65) Prior Publication Data

US 2006/0209256 A1 Sep. 21, 2006

Related U.S. Application Data

(63) Continuation of application No. PCT/EP2004/009921, filed on Sep. 6, 2004.

(30) Foreign Application Priority Data

Sep. 12, 2003 (DE) ................................ 103 42 175

(51) Int. Cl.
*G01B 9/02* (2006.01)
(52) U.S. Cl. .................. 356/73; 356/511; 356/515
(58) Field of Classification Search ................ 356/73, 356/511–515, 521; 351/211, 221
See application file for complete search history.

(56) References Cited

U.S. PATENT DOCUMENTS

| 5,673,096 | A | * | 9/1997 | Dorsel et al. ............... 351/211 |
| 5,973,781 | A | * | 10/1999 | Moeller et al. ............. 356/495 |
| 7,084,986 | B2 | * | 8/2006 | Hellmuth et al. ........... 356/479 |
| 2001/0016695 | A1 | | 8/2001 | Mihashi et al. |
| 2002/0163623 | A1 | | 11/2002 | Hirohara et al. |
| 2003/0038921 | A1 | | 2/2003 | Neal et al. |
| 2003/0169403 | A1 | | 9/2003 | Curatu |

FOREIGN PATENT DOCUMENTS

DE        197 13 138 A1    10/1998

* cited by examiner

*Primary Examiner*—Samuel A. Turner
(74) *Attorney, Agent, or Firm*—Laurence A. Greenberg; Werner H. Stemer; Ralph E. Locher

(57) ABSTRACT

A device and a method are used for measuring the surface topography and a wave aberration of a lens system. The device is fitted with a first measuring system containing a light source radiating a first light beam of a first wavelength, and a detector which captures the first light beam which is reflected on the lens system. In addition the device has a second measuring system containing a light source for radiating a second light beam of a second wavelength and a detector for capturing the second light beam transmitted by the lens system. A diffractive optical element is disposed in a common beam path of the first measuring system and second measuring system. The optical element adapts the respective wave-front course of the first light beam and the second light beam in a wavelength-selective manner.

22 Claims, 4 Drawing Sheets

DEVICE AND METHOD FOR MEASURING SURFACE TOPOGRAPHY AND WAVE ABERRATION OF A LENS SYSTEM, IN PARTICULAR AN EYE

CROSS-REFERENCE TO RELATED APPLICATION

This application is a continuation, under 35 U.S.C. § 120, of copending international application No. PCT/EP2004/009921, filed Sep. 6, 2004, which designated the United States; this application also claims the priority, under 35 U.S.C. § 119, of German patent application No. 103 42 175.0, filed Sep. 12, 2003; the prior applications are herewith incorporated by reference in their entirety.

BACKGROUND OF THE INVENTION

Field of the Invention

The invention relates to a device for measuring a surface topography ("topography" for short below) and wave aberration of a lens system. The device has a first measuring system that contains a light source for emitting a first light bundle of a first wavelength, a detector for picking up the first light bundle reflected at the lens system, a second measuring system that contains a light source for emitting a second light bundle of a second wavelength and a detector for picking up the second light bundle transmitted through the lens system. Such a device can be used in principle for measuring any type of optical lens system. Such a device is used, however, in particular in optical medical technology. The lens system to be examined is in this case an eye (a human one, in particular). The invention relates furthermore to an associated method.

The ablation of cornea tissue by excimer lasers has recently been used increasingly for operations on the human eye such as, for example, the correction of defective vision of the eye. For this purpose, a flap-like layer of the cornea is cut open and folded to the side. Thereupon a suitable amount of tissue is ablated (that is to say removed) at the cornea tissue lying open, and the cornea flap is replaced again thereafter. In this way, the cornea is specifically deformed in such a way as to compensate for defective vision of the eye, for example near or far sightedness or astigmatism. In order to be able to calculate sufficiently accurately the quantity of cornea tissue to be removed, there is a need for detailed knowledge both of the wave aberration, that is to say the defective optical imaging of the eye, and of the topography of the cornea.

A similar information density is also required for other correction methods on the human eye, for example the transplantation of the cornea, the exchange of the eye lens for an artificial lens, or the adaptation of a contact lens.

To date, the topography of the cornea and the wave aberration of the eye have usually been measured separately. This frequently gives rise to discrepancies between the two measurements carried out in temporal sequence, because of the instability of the eye as a biological object, on the one hand, and because of the numerous degrees of freedom of adjustment of the eye relative to the measuring device, on the other hand. For application in optical medicine, such a measuring discrepancy can, in particular, impair the success of an operation on the eye, or of some other medical correction method.

In order to avoid such discrepancies, it is therefore desirable to measure the topography and the wave aberration simultaneously. This is enabled per se in a measuring method known from U.S. patent disclosure No. 2002/0163623 A1. According to the known method and the associated device, two measuring systems are provided that emit light signals at different wavelengths and capture them again after reflection at the eye or at the cornea. In the known device, it is possible to implement the beam guidance of the light bundles required for both measurements only with a comparatively large outlay. This conversely limits the precision of the measurements.

A similar measuring method is further disclosed in U.S. patent disclosure No. 2001/0016695 A1.

SUMMARY OF THE INVENTION

It is accordingly an object of the invention to provide a device and a method for measuring the surface topography and wave aberration of a lens system, that overcomes the above-mentioned disadvantages of the prior art devices and methods of this general type.

With the foregoing and other objects in view there is provided, in accordance with the invention, a device for measuring a topography and a wave aberration of a lens systems. The device contains a first measuring system having a first light source for emitting a first light bundle of a first wavelength and a first detector for picking up the first light bundle reflected at the lens system. The device further contains a second measuring system having a second light source for emitting a second light bundle of a second wavelength and a second detector for picking up the second light bundle transmitted through the lens system. A diffractive optical element is disposed in a common beam path region of the first and second measuring systems. The diffractive optical element adapts a respective wave-front profile of the first light bundle and of the second light bundle in a wavelength-selective fashion.

Accordingly, there is disposed in the common beam path region of a first and of a second measuring system the diffractive optical element (that is to say one that causes light diffraction) that adapts the respective wave-front profile of a first light bundle and of a second light bundle in a wavelength-selective fashion.

The term wave-front profile is used for the function of the three-dimensional space that describes the spatial alignment of a surface perpendicular to the local direction of light propagation at every location within the beam path of the respectively considered light bundle. The diffractive optical element (DOE) acts in a wavelength-selective fashion to the extent that the wave-front profile of the two light bundles is influenced in a different way because of their different wavelengths when traversing the DOE.

The use of the DOE and of the wavelength-selective beam guidance enabled thereby permits the wave-front profile of the two light bundles to be adapted flexibly, quasi-independently and with high precision to the requirements of the respective measurement.

In a preferred embodiment of the invention, the DOE is configured in such a way that the zeroth diffraction order of the first light bundle is suppressed, that is to say its intensity is completely nullified or at least greatly reduced. The light of the first light bundle is, on the contrary, predominantly or completely transmitted into the first diffraction order. At the same time, as a result of a suitable configuration of the DOE, the latter exerts in essence no diffracting action on the light of the second light bundle. The second light bundle is therefore transmitted substantially unattenuated into the zeroth diffraction order.

By a suitable configuration of the DOE, the wave-front profile of the first light bundle transmitted by the DOE in the direction of the lens system is expediently preadapted to the topography of the lens system. Preadaptation is understood, in particular, to mean that the wave-front profile of the first light bundle is deformed by the DOE in such a way that the curvature of the wave-fronts at the location of the lens system correspond approximately to its surface curvature. This has the advantage that the light of the first light bundle impinges on the surface of the lens system in a substantially perpendicular fashion overall, and is approximately retroreflected into itself. In this way, even slight deviations in the topography of the lens system from the preadaptation can be detected precisely. Moreover, the preadaptation of the wave-front profile reduces the light loss through scattered light. When applying the invention to the human eye as lens system to be tested, the DOE is preferably fashioned in such a way that the wave-front profile of the first light bundle is adapted to a medical standard model of the human eye, in particular the Gullstrand normal eye. With regard to the second light bundle, by contrast, the DOE is preferably configured in such a way that its wave-front profile is substantially unmodified.

A surface-corrugated phase element is particularly suitable as DOE. This is understood to be a plate made from glass or a transparent plastic into the surface of which a relief-type diffraction grating is introduced. Such a phase element can nowadays be produced with extremely high precision in a comparatively cost-effective way by computer-aided production methods and suitable etching techniques. The diffraction action of the phase element can thereby be adapted in a highly flexible way to what is needed. It is possible in particular to use a surface-corrected phase element to achieve a surface grating with an extremely small grating period of the order of magnitude of a few hundred nanometers, and thus a comparatively large deflection angle of the diffracted light. However, it is conceivable in principle to implement the DOE in another way, for example by a volume hologram or a reflective diffractive element. In particular, it is also conceivable to configure the DOE as a flexible optical element that can be freely driven. This is possible, for example, by a phase-shifting liquid crystal displays (LCD).

In order to fix the refractive power and the alignment of an eye to be examined during the duration of the measurement, and thus to increase the measuring accuracy, it is preferably provided to insert a fixation target into the eye by a third light bundle. A fixation target is understood as an image that is offered for viewing to a test subject to be examined during measurement. By aiming at the fixation target, the test subject automatically keeps constant to a good approximation both the orientation of the eye and the refractive power set by the eye. The third light bundle used for inserting the fixation target has a third wavelength for which the DOE is preferably likewise inactive. The third wavelength is preferably different both from the first wavelength and the second wavelength. It is ensured in this way that the third light bundle influences the measurement of neither the topography nor the wave aberration. In a simplified configuration of the inventive device, however, it is provided as an alternative that the third wavelength corresponds to the second wavelength.

The two measuring systems share a common detector in a particularly rational variant of the device.

In order to achieve a large diffraction angle and to prevent the light bundle from dazzling the test subject to be examined during the measurement, the wavelengths of the first and/or second light bundle(s) preferably lie in the long wave and near infrared region, not visible to the human eye, of the electromagnetic spectrum. The first wavelength is selected, in particular, approximately in the range between 1000 nm and 1600 nm. The second wavelength preferably corresponds to a coarse approximation to half the first wavelength. The second wavelength correspondingly lies in the boundary region between the visible nd green spectral region and the near infrared region.

In order to avoid measuring errors caused by a maladjustment of the lens system with reference to the DOE, the device expediently contains an adjusting configuration with the aid of which the position of the lens system can be determined and set. A particularly advantageous implementation of such an adjusting configuration contains a light source and a position-sensitive detector. In order to adjust the lens system, an adjusting light beam is cast by the light source onto the lens system at an angle, and the adjusting light beam reflected thereat is captured on the position-sensitive detector. In order to adjust the lens system, the position of the lens system is now varied with reference to the DOE until the reflected adjusting light beam impinges at a predetermined point of the detector surface that indicates the correct adjustment of the lens system with reference to the DOE.

It is advantageous for a particularly precise adaptation of the wave-front profile of the light bundles when the DOE is directly upstream of the lens system such that the light of the light bundle emanating from the DOE falls directly onto the lens system. Conversely, the light of the light bundle that is retroreflected by the lens system again falls directly onto the DOE before it is led to the detectors of the two measuring systems.

As a result of a wavelength-selective beam splitter that limits the common beam path region of the two measuring systems, the two light bundles are fed effectively to the respective detector after reflection at the eye. As a result, an undesired interaction of the two measuring systems that could lead to a falsification of the measurement result is avoided, in particular. In an expedient embodiment of the invention, such a beam splitter is configured, in turn, as a diffractive optical element that separates the beam path of the two light bundles from one another in a wavelength-selective fashion.

A so-called wave-front detector is suitable as the detector of the first and/or the second measuring system. This is understood as a detector that detects the spatial alignment of a wave-front. The use in particular of a Shack-Hartmann sensor or an interferometer, for example of shearing type, as the detector of the first and/or second measuring system is provided within the scope of the device according to the invention. A pyramidal sensor or a Talbot interferometer can, furthermore, advantageously be used within the scope of the device according to the invention.

In the course of the method carried out with the aid of the device according to the invention, it is preferred to measure the topography and the wave aberration simultaneously. A particularly short measuring time is thereby achieved. This, in turn, is of advantage in particular when applying the method to the human eye, all the more so as a test subject to be examined has to keep still as much as possible during the measurement, and this necessarily entails a certain unpleasantness. On the other hand, the simultaneous measurement of topography and wave aberration prevents discrepancies between the respective result of these two measuring methods which would occur owing to the instability of the human eye for measurements separated in time.

A temporally sequential measurement, that is to say one that is offset in time (in particular at a very short interval) is, nevertheless, regarded as an advantageous alternative with regard to a simplified conduct of the method. Particularly when use is made of a common detector for both measuring systems, this is sensible in order to separate the measuring signals of the two measuring systems more effectively. In order to avoid measuring discrepancies, the measurements are preferably carried out in a time interval that is less than the reaction time of the eye so that the measurements is conducted quasi-simultaneously with regard to the eye.

In an expedient alternative embodiment of the method according to the invention, the topography and/or the wave aberration are/is measured with the aid of a so-called scanning spot method. In this inherently conventional measuring technique, the lens system is not illuminated with a flat light bundle, but is scanned with a fine light beam of approximately punctiform cross section. Accordingly, in the case of a scanning spot method it is not the wave-front profile of the light reflected by the lens system that is measured, but the deflection of the reflected thin light beam from a desired position characteristic of an "ideal lens system". A customary wave-front method and a scanning spot method are equivalent with regard to the information content relating to the topography or the wave aberration of the lens system being examined.

Other features which are considered as characteristic for the invention are set forth in the appended claims.

Although the invention is illustrated and described herein as embodied in a device and a method for measuring the surface topography and wave aberration of a lens system, in particular an eye, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

DESCRIPTION OF THE PREFERRED EMBODIMENTS

Figure 1:
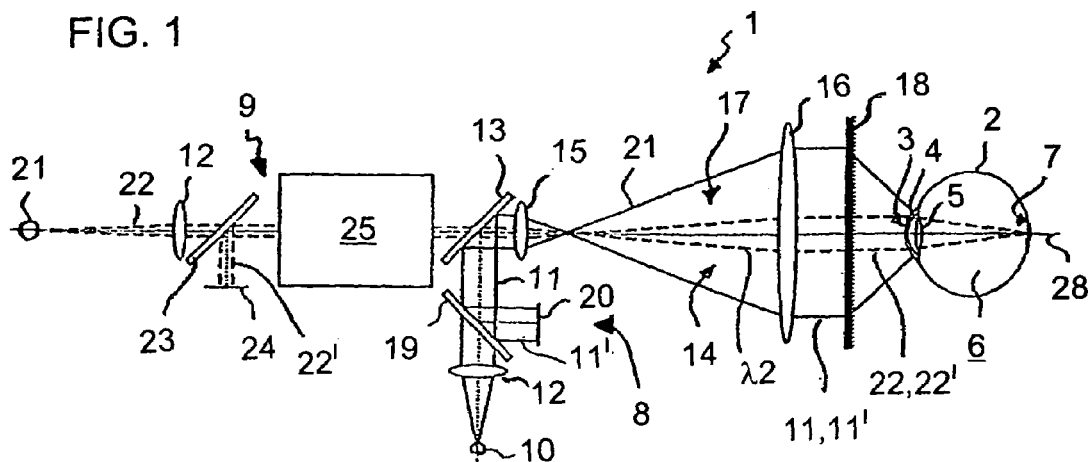
FIG. 1 is a diagrammatic illustration of a device for measuring a topography and wave aberration of a lens system, in particular the human eye, having a diffractive optical element (DOE) disposed in a common beam path region of a first measuring system and a second measuring system according to the invention.

In all the figures of the drawing, sub-features and integral parts that correspond to one another bear the same reference symbol in each case. Referring now to the figures of the drawing in detail and first, particularly, to FIG. 1 thereof, there is shown a schematic illustration of a device 1 for measuring the topography and wave aberration of a lens system. The term lens system here includes any artificial or natural optical system equipped with one or more lenses. The lens system illustrated schematically in FIG. 1 is, in particular, a human eye 2.

The three-dimensional shape of the lens surface is denoted as (surface) topography. In the case of the eye 2, a lens surface is a surface 3 of a cornea 4. The lens system of the eye 2 further contains in a known way an eye lens 5 and a vitreous body 6. A retina 7 is disposed in a known way in the fundus of the eye opposite the eye lens 5.

The term wave aberration denotes in general the deviation of the optical imaging properties of the real lens system to be tested from the imaging properties of a corresponding ideal lens system. In the case of the eye 2, the wave aberration contains first order aberrations such as near sightedness, far sightedness or astigmatism, as well as higher order aberrations.

The device 1 is provided with a first measuring system 8 for measuring the topography of the cornea 4. A second measuring system 9 is provided for measuring the wave aberration.

The first measuring system 8 contains a light source 10, in particular a laser. The light source 10 produces a first light bundle 11 of a first wavelength $\lambda 1$. The light bundle 11 is first directed in parallel in a collimator lens 12 along the beam path of the first measuring system 8 and irradiated into a common beam path region 14 of the measuring systems 8 and 9 by a wavelength-selective beam splitter 13. Within the beam path region 14, the first light bundle 11 is expanded by a Kepler telescope 17 formed of two lenses 15 and 16, and traverses a diffractive optical element (DOE) 18 directly upstream of the eye 2. The first light bundle 11 is collimated in the direction of the eye 2 by the DOE 18, whose mode of operation is described in more detail below. A component of the light bundle 11 incident on the eye 2 (denoted below as reflected light bundle 11' for the sake of simplicity) is reflected at the surface 3 of the cornea 4 and retroreflected against the direction of incidence through the DOE 18, the Kepler telescope 17 and the beam splitter 13. The reflected light bundle 11' is coupled out of the incident light bundle 11 and led to a wave-front detector 20 by a further beam splitter 19 disposed outside the common beam path region 14. The Kepler telescope 17 is configured here in such a way that the cornea 4 is imaged sharply on the wave-front detector 20. The wave-front detector 20 is optionally configured as a Shack-Hartmann sensor, as is described in U.S. patent disclosure No. 2003/0038921 A1, for example. Alternatively, the wave-front detector 20 can also be configured as an interferometer, in particular a shearing interferometer.

The second measuring system 9, provided for measuring the wave aberration, contains a further light source 21. The light source 21, which is preferably implemented, in turn, by a laser, emits a second light bundle 22 of a second wavelength $\lambda 2$ in the form of a comparatively fine light bundle. The second light bundle 22 is once again directed in parallel in a collimator lens 12 and irradiated through the wavelength-selective beam splitter 13 into the common beam path region 14. Because of its wavelength selectivity, the beam splitter 13 is transparent to the wavelength λ2, and therefore inactive. A beam splitter 13 having such wavelength selectivity can be produced according to a conventional technique by a dielectric mirror, for example.

In the further course of its beam path, the second light bundle 22 falls through the Kepler telescope 17 and the DOE 18 onto the eye 2. In a manner described in more detail below, the DOE 18 is thereby fashioned in such a way that it has no diffracting action, or only a negligible one, on light of wavelength λ2. The light bundle 22 consequently traverses the DOE 18 in a quasi-unmodified fashion and falls onto the retina 7 as a further fine light bundle through the cornea 4 and the eye lens 5. The light bundle 22 is backscattered diffusely at the retina 7. The scattered light, denoted below as backscattered light bundle 22', falls back against its direction of incidence through the eye lens 5, the cornea 4, the DOE 18, the Kepler telescope 17 and the beam splitter 13 transparent to the wavelength λ2. A further beam splitter 23 positioned outside the common beam path region 14 in the beam path of the light bundle 22, 22' couples out the backscattered light bundle 22' and casts it onto a wave-front detector 24 of the second measuring system 9. The wave-front detector 24 is, in turn, optionally configured as a Shack-Hartmann sensor or as an interferometer. A precompensation unit 25 is interposed between the beam splitters 13 and 23. The precompensation unit 25 includes a conventional non-illustrated optical zoom system or a lens configuration with the aid of which it is possible to compensate the components of defocus and astigmatism, that is to say the near or far sightedness and astigmatism. The precompensation unit 25 serves conversely also for the purpose of imaging the incident light bundle 22 sharply on the retina 7.

Other than in the case of the eye 2, the wave aberration can be measured in general in a simplified fashion for an artificial lens system by disposing the lens system between the light source and detector such that the lens system is transluminated only once by the second light bundle.

Figure 2:
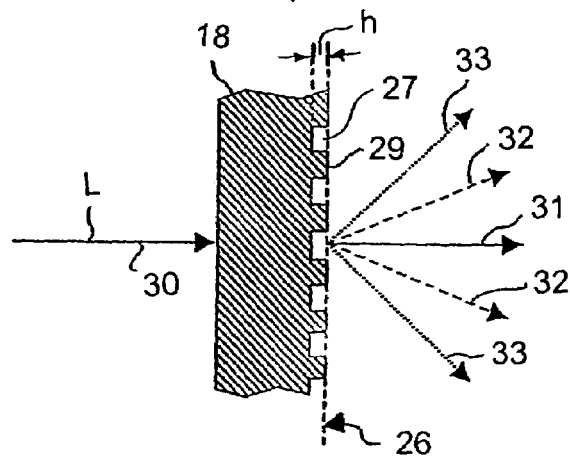
FIG. 2 is a diagrammatic, cross-sectional view showing the diffractive optical element in accordance with FIG. 1.

The DOE 18 illustrated in FIG. 1 is a so-called surface-corrugated phase element whose configuration and mode of operation are sketched schematically in FIG. 2. The DOE 18 depicted is a platelet made from glass or a transparent plastic and into a surface 26 of which facing the eye 2 there is introduced a relief-type diffraction grating. The diffraction grating of the DOE 18 contains a number of depressions 27 that are approximately of annular shape and disposed approximately concentrically about the optical axis 28 (FIG. 1) of the device 1, and are separated from one another by interposed webs 29. The depressions 27 and the interposed webs 29 can deviate in a predetermined way from the spherical shape and concentric configuration in order to achieve aspheric diffraction patterns.

As is to be seen from FIG. 2, preferably all the depressions 27 have the same structural depth h such that the surface 26 is subdivided into two discrete levels. A DOE configured in such a way is also denoted as a binary hologram.

With regard to their optical action, the depressions 27 and webs 29 of the relief-type surface 26 form alternating phases within which an incident plane light wave L develops differently as a consequence of the difference in refractive index between the material of the DOE 18 and the ambient air. As a result, upon traversal of the light wave L through the surface 26, a phase difference arises between partial waves in the region of the depressions 27 and partial waves in the region of the webs 29 that lead in a way known per se to interference effects and diffraction effects.

These effects have the consequence that when exiting from the DOE 18 the irradiated light wave L emits only in discrete directions with reference to the direction of incidence 30. The partial beams emitted in these discrete directions are denoted as diffraction orders 31, 32, 33. In general, a portion of the irradiated intensity of radiation is emitted without diffraction, that is to say in the direction of incidence 30. This partial radiation is denoted as zeroth diffraction order 31. The further diffraction maxima are denoted as first diffraction order 32, second diffraction order 33, etc. as angle increases with reference to this zeroth diffraction order 31. For reasons of simplicity, higher diffraction orders are not illustrated in the schematic in accordance with FIG. 2.

The angles at which the individual diffraction orders 32, 33, etc. appear with reference to the zeroth diffraction order 31 are a function of the grating constant of the diffraction grating, that is to say the spacing between two neighboring depressions 27. The diffraction angles are larger here the smaller the grating constant.

It can be disposed for the irradiated light to be preferably emitted into a specific diffraction order 31, 32 or 33 by a suitable configuration of the DOE 18 with regard to the wavelength of the irradiated light wave L. This is utilized according to the invention by tuning the diffraction grating of the DOE 18 with wavelengths λ1 and λ2 for wavelength-selective adaptation of the wave-front profile of the light bundles 11 and 22.

Here, the DOE 18 is tuned to the wavelength λ1 in such a way that partial waves of the light bundle 11 in the region of the depression 27 on the one hand, and in the region of the web 29, on the other hand, pierce the surface 26 precisely in a fashion offset by an odd multiple of the half wavelength, and thus interfere negatively in the direction of incidence 30, that is to say along the optical axis 38. This condition is fulfilled whenever the structural depth h satisfies the equation $$h = i \cdot \frac{\lambda_1}{2 \cdot (n(\lambda_1) - 1)}, \qquad \text{Equation 1}$$

where $n(\lambda_1)$ being the refractive index of the material of the DOE 18 for the wavelength $\lambda_1$ and i=1,3,5 . . . being an odd, natural number.

Furthermore, the DOE 18 is fashioned such that the surface area occupied by the depression 27 corresponds substantially to the surface area of an adjoining web 29. As a result of this, the zeroth diffraction order 31 of the first light bundle 11 is suppressed almost completely by destructive interference.

Figure 3:
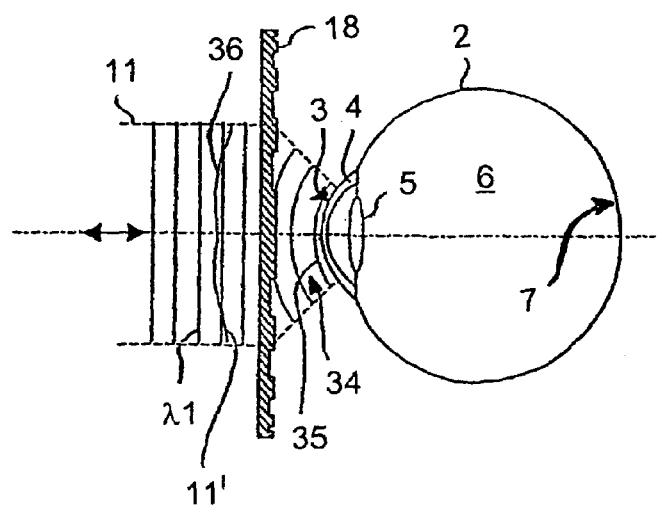
FIG. 3 is a diagrammatic, sectional view of the diffractive optical element and the eye in the beam path of a first light bundle for measuring the topography of the eye.

As is to be seen from FIG. 3, when the light bundle 11 illuminates the DOE 18, a curved wave-front profile 34 is formed in the region of the eye 2 owing to the previously described diffraction effect. By suitably varying the grating spacing of the DOE 18, the wave-front profile 34 is preadapted to the eye 2 such that the curvature of the wavefronts 35 in the region of the cornea 4 corresponds to the average surface curvature of the human cornea. The DOE 18 is optionally formed in such a way that the curved wave-front profile 34 corresponds to a spherical wave. A spherical wave includes, in particular, a focus with the aid of which the entire measuring system 8 can be calibrated in a comparatively simply way. In order to preadapt an aspheric deviation of the cornea surface with comparatively simple measures, the DOE 18 is alternatively formed in such a way that the curved wave-front profile 34 corresponds to a spherical wave with a conical component adapted to the cornea 4. Alternatively, it is provided in turn for the DOE 18 to be formed in such a way that the shape of the wave-fronts 35 at the location of the cornea 4 corresponds to the average shape of the cornea 4 to be derived from the standard eye model of Gullstrand.

Were the topography of the cornea 4 to correspond exactly to the preadaptation, in particular to the curvature described by the Gullstrand normal eye, the light bundle 11 would impinge exactly vertically on the surface 3 of the cornea 4 and be retroreflected exactly into itself onto the DOE 18. In reversal of the above-described diffraction effect, in this ideal case the DOE 18 would transform the curved wave-front profile of the reflected light bundle 11' into a plane wave that would correspond exactly to the incident light bundle 11.

The topography of the cornea 4 of the real eye 2 is, however, individually different and, in particular, deviates more or less strongly from the Gullstrand normal eye. Consequently, the wave-front profile 34 of the light bundle 11 is distorted upon reflection at the surface 3. Consequently, upon traversing the DOE 18 the reflected light bundle 11' is converted into a wave-front 36 that is curved by comparison with the incident plane wave-front. The curvature of the wave-front 36 is detected in the wave-front detector 20. The topography of the cornea 4 can be calculated therefrom with the aid of computational methods known per se.

On the other hand, the DOE 18 is tuned to the wavelength $\lambda 2$ in such a way that the second light bundle 22 is preferably transmitted into the zeroth diffraction order 31. This is always the case when a phase difference that is an integral multiple of the full wavelength $\lambda 2$ is reached between the depressions 27 and adjacent webs 29. The condition for this is that the structural depth of the equation $$h = j \cdot \frac{\lambda_2}{(n(\lambda_2) - 1)} \qquad \text{Equation 2}$$

is sufficient, $n(\lambda_2)$ being the refractive index of the material of the DOE 18 for the wavelength $\lambda 2$, and $j=1,2,3,\ldots$ being a natural number.

Figure 4:
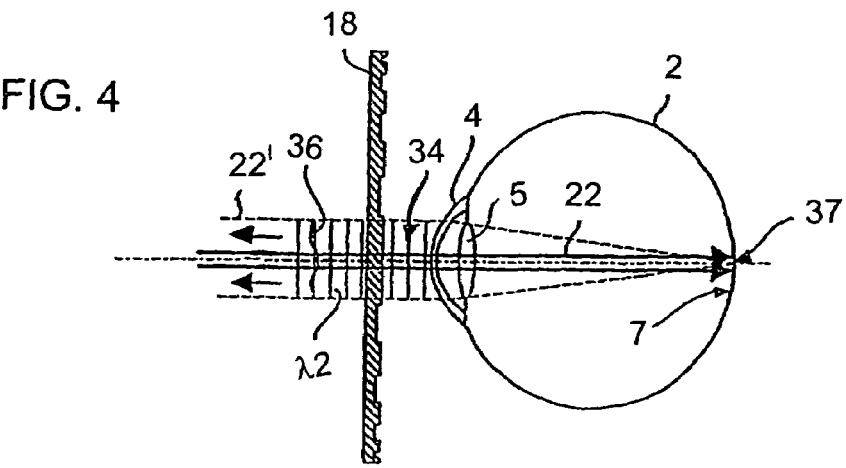
FIG. 4 is a diagrammatic, sectional view of the diffractive optical element and the eye in the beam path of a second light bundle for measuring the wave aberration of the eye, in an illustration in accordance with FIG. 3.

As may be seen from FIG. 4, if this condition is fulfilled the wave-front profile 34 of the light bundle 22 is virtually not modified during passage through the DOE 18. The DOE 18 is therefore substantially inactive for the light bundle 22.

The measurement of the wave aberration of the eye is performed in accordance with FIG. 4 in such a way that an approximately punctiform spot 37 is illuminated on the retina 7 with the aid of the light bundle 22 formed as a fine beam. The light bundle 22' diffusely backscattered by the spot falls back through the eye lens 5 and the cornea 4 onto the DOE 18 and is transmitted from there in the direction of the wave-front detector 24.

As a consequence of its slight beam cross section, the incident light bundle 22 is influenced by the wave aberration of the eye 2 only to a comparatively slight extent. However, on the return path the backscattered light bundle 22' penetrates the full cross-sectional surface of the eye pupil and consequently collects the entire information relating to the wave aberration of the eye 2.

Whereas in the case of an ideal imaging characteristic of the eye 2, that is to say given a vanishing wave aberration, it would be expected that the light bundle 22' emanating from the illuminated spot 37 as a quasi punctiform light source ought to be imaged by the (relaxed) eye 2 into a plane wave with parallel wave-fronts, the wave-fronts 36 of the light bundle 22' are curved, very much as a rule, by the non-vanishing wave aberration of the real eye 2. This curvature is precompensated in a first order (by correcting near sightedness, far sightedness or astigmatism) in the precompensation unit 25. The higher order curvature, remaining after the precompensation, of the wave-front 36 is detected by the wave-front detector 24. Methods known per se are used to calculate the wave aberration of the eye 2 therefrom.

The wavelengths $\lambda 1$ and $\lambda 2$ are selected for the purpose of achieving larger diffraction angles, preferably in the comparatively longwave infrared region. The invisible infrared light has the advantage, in addition, that both the topography and the wave aberration can be measured without this being noticed by the test subject. Consequently, in particular, the test subject is prevented from being dazzled by the light bundles 11 and 22, or from reacting to the irradiation of light in a way that impairs the measurement. Advantageous wavelength combinations are, in particular, $\lambda 1 = 1550$ nm and $\lambda 2 = 785$ nm. On the other hand, from the point of view of better availability of sensitive and comparatively cost-effective light sensors, the selection of smaller wavelengths for the first light bundle 11 and/or the second light bundle 22 is also advantageous; in particular, $\lambda 1 = 1064$ nm and/or $\lambda 2 = 532$ nm. It is preferred to measure the topography and the wave aberration simultaneously, but the measurements can also be carried out individually or sequentially with a time offset.

Figure 5:
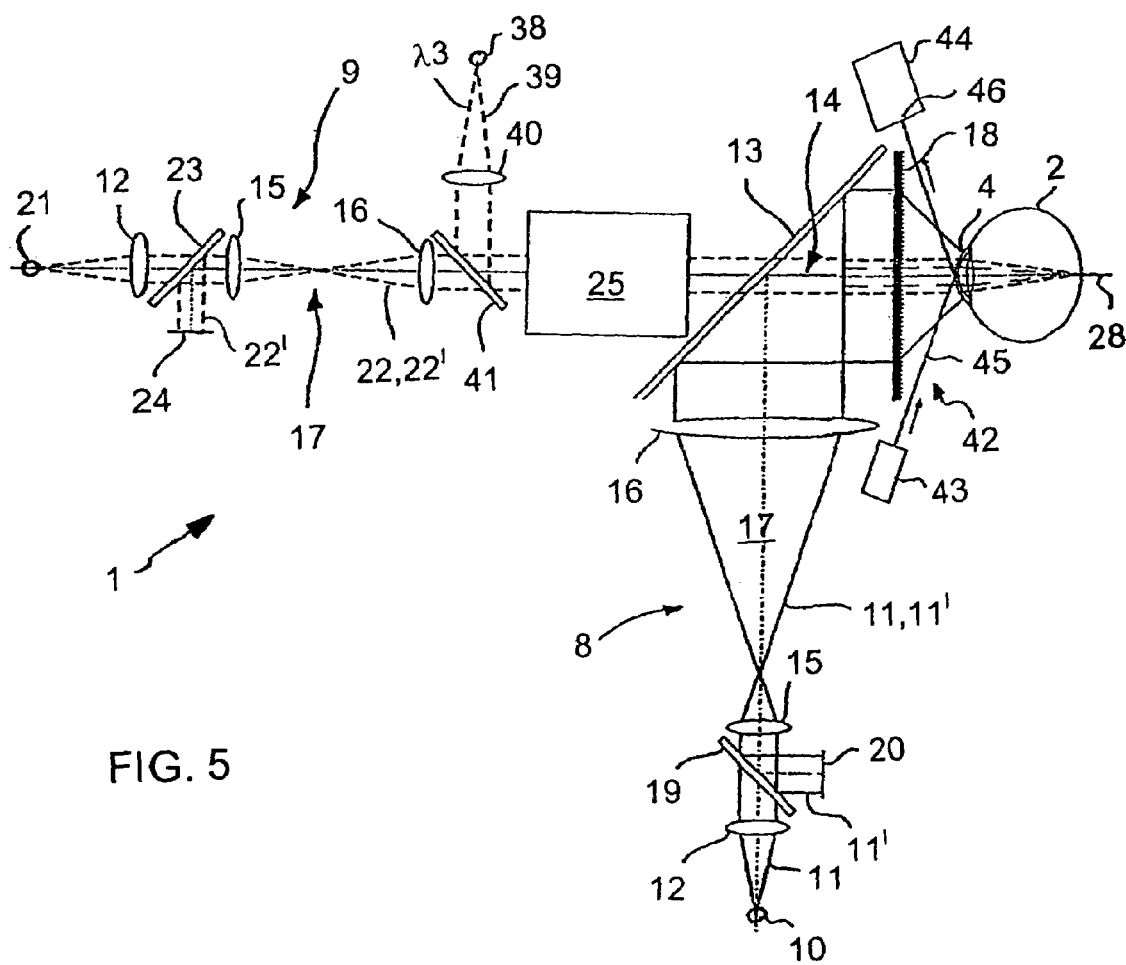
FIG. 5 is a diagrammatic, illustration of an alternative configuration of the device in an illustration in accordance with FIG. 1.

FIG. 5 shows an alternative embodiment of the device 1. This embodiment differs from the configuration in accordance with FIG. 1 in that here the beam splitter 13 directly follows the DOE 18. Therefore, it is not until immediately before they fall onto the DOE 18 that the light bundles 11 and 22 are combined in the common beam path region 14 and the light bundles 11', 22' are separated on the return path directly after traversing the DOE 18. For the purpose of expanding or imaging the light bundles 11, 11' and 22, 22', one Kepler telescope 17 each is disposed outside the common beam path 14 in the beam path of the two light bundles 11, 11' and 22, 22'.

In the configuration in accordance with FIG. 5, the device 1 contains a third light source 38 by which a third light bundle 39 of a third wavelength $\lambda 3$ can be inserted into the eye 2. The third light bundle 39 is, in turn, directed in parallel by a collimator lens 40 and aligned by a wavelength-selective beam splitter 41 with the optical axis 29 and thus with the eye 2. The third light bundle 39 serves the purpose of offering the eye 2 a so-called fixation target. This is understood as an image at which the test subject aims during the measurement. First, aiming for the fixation target results in that the viewing axis of the eye 2 is aligned along the optical axis 28. Second, the refractive power of the eye lens 5 is fixed in a range in which the test subject can sharply detect the fixation target. In particular an image at infinity is frequently simulated for the test subject by the fixation target such that the eye lens 5 is held in the relaxed state during the measurement. The third light bundle 39 likewise traverses the precompensation unit 25 in order, in particular, to compensate any possible shortsightedness of the eye 2, and so to give the test subject the actual possibility of sharply aiming at the fixation target. The wavelength $\lambda 3$ of the third light bundle 39 must necessarily be in the visible spectral region, and is preferably selected in such a way that the DOE 18 does not exert any diffracting action on the light bundle 39. So as to simplify the measuring setup, the third wavelength $\lambda 3$ can therefore also be selected, in particular, to be equal to the second wavelength λ2. In this case, the third light bundle 39 is blocked out briefly during the measurement of the wave aberration. Alternatively, the third wavelength λ3 can also, however, be selected in such a way that the DOE 18 suppresses the zeroth diffraction order 31 of the third light bundle 39.

So-called maladjusting aberrations can also be caused by a false positioning of the eye 2 with reference to its lateral and axial position in relation to the DOE 18. The eye 2 must therefore be adjusted exactly with reference to the device 1 before measurement is begun. In a way similar to conventional measuring devices of optical medicine, the test subject is fixed for the measurement with reference to the device 1 by bearing surfaces (not illustrated in more detail) for chin and forehead. Since the dimensions of the head vary from test subject to test subject, however, a fine adjustment of the device 1 with reference to the fixed head of the test subject is required for correct positioning of the eye 2. An adjusting configuration 42 that includes a light source 43 and a position-sensitive detector 44 and is illustrated schematically in FIG. 5 serves the purpose of facilitating this adjusting operation. The light source 43, which is, in particular, a laser, casts obliquely onto the eye 2 a fine adjusting light beam 45 that is reflected at the cornea 4 in the direction of the position-sensitive detector 44. With correct adjustment of the eye 2, the adjusting light beam 45 impinges at a predetermined point on the detector 44. By contrast, if the eye 2 is maladjusted, the reflected adjusting light beam 45 impinges at a point differing therefrom or—given coarse maladjustment of the eye 2—does not impinge on the detector 44 at all. Before measurement is started, the position of the device 1 is therefore adjusted with reference to the eye 2 until the point of impingement of the reflected adjusting light beam 45 corresponds to the predetermined point 46 on the detector 44. In the simplest case, the detector 44 is a viewing screen on which the point of impingement of the adjusting light beam can be observed by eye. However, the detector 44 can also be an electronic detector, in particular a CCD sensor.

Figure 6:
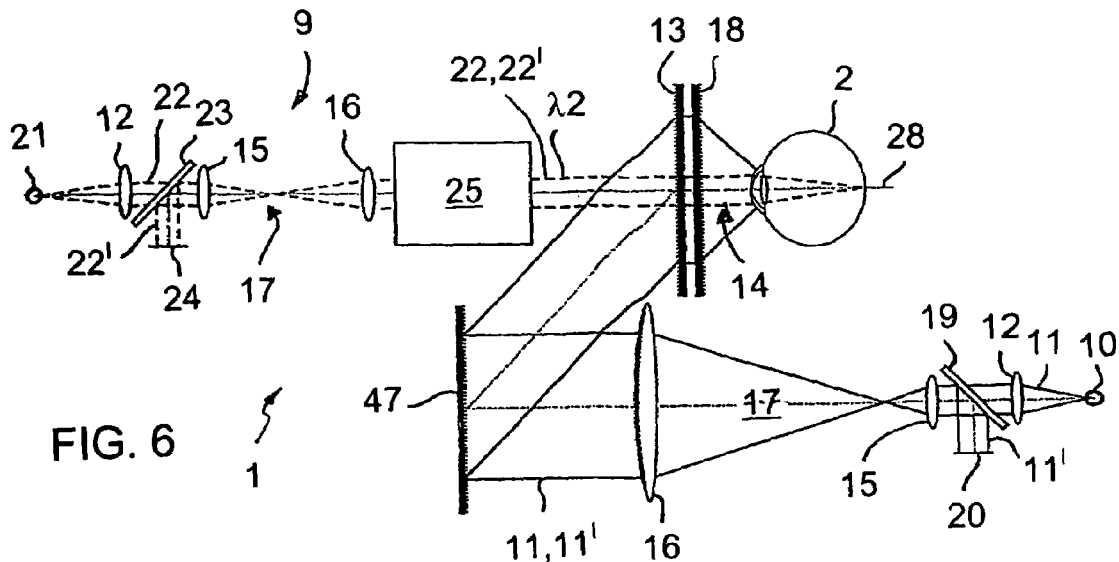
FIGS. 6 to 8 are diagrammatic, illustrations showing further embodiments of the device in an illustration in accordance with FIG. 1.

A further embodiment, illustrated in FIG. 6, of the device 1 differs from the above-described configurations in that the wavelength-selective beam splitter 13 is likewise configured as a diffractive optical element. In the same way as the DOE 18, the beam splitter 13 in this case selectively diffracts the wavelength λ1, while light of wavelength λ2, in particular the light bundle 22, transmits the beam splitter 13 undiffracted. The beam splitter 13 has a surface structure or volume structure in the form of a regular linear grating, as a result of which the beam path of the first light bundle 11, 11' is deflected by a defined angle. The beam splitter 13 and the DOE 18 can thereby also be united in a single optical element. The beam path of the light bundle 11, 11' is deflected again into a direction parallel to the optical axis 28 by a further DOE 47. By contrast with the beam splitter 13 and the DOE 18, the DOE 47 is hereby configured as a reflective element, in particular as a sawtooth prism.

Figure 7:
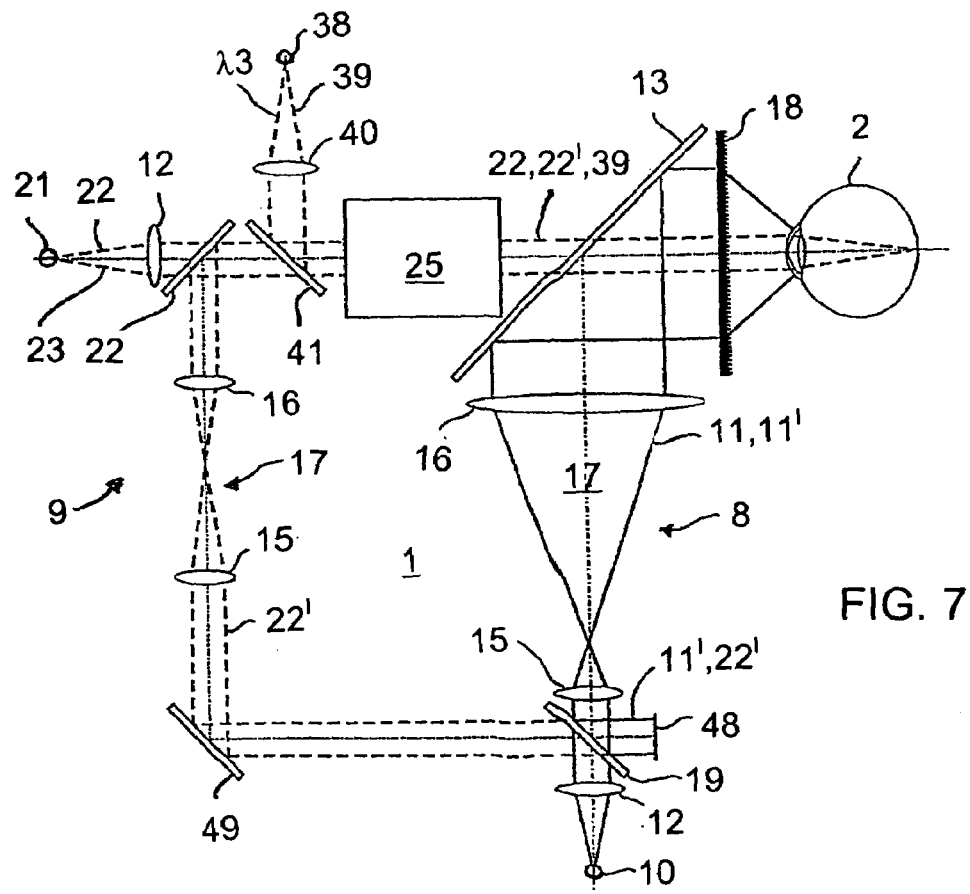
Figure 8:
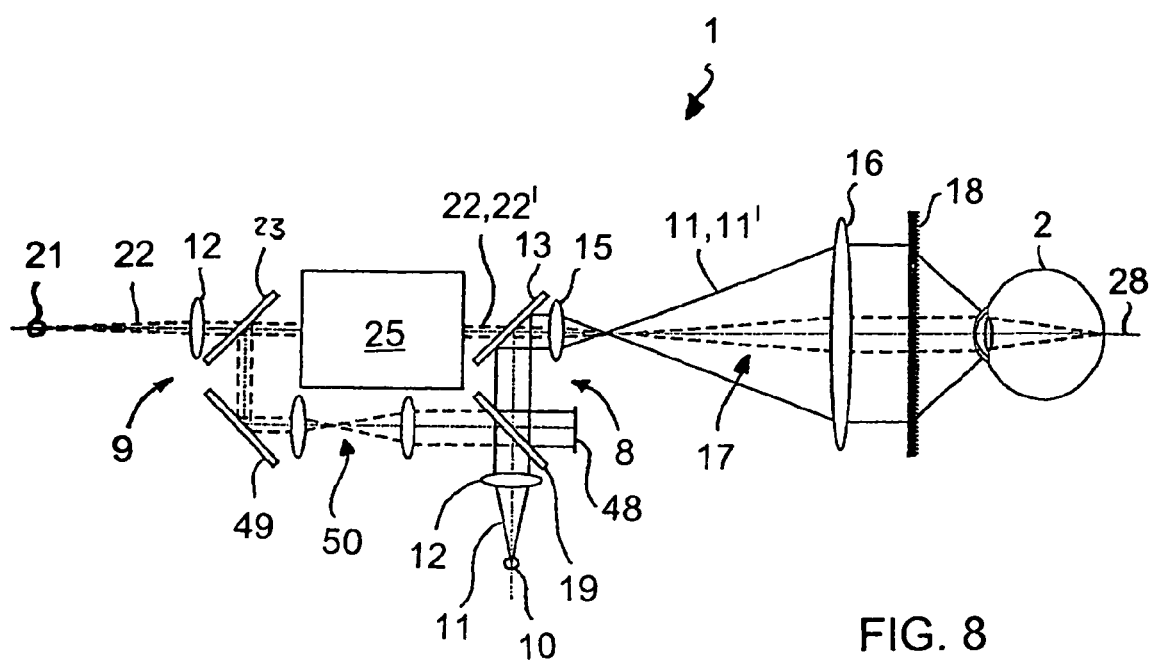

A common detector 48 for both measuring systems 8 and 9 is provided in the further variants of the device 1 that are illustrated in FIGS. 7 and 8. This particularly rational configuration is rendered possible by the fact that, after being coupled out of the optical axis 28 by a mirror 49, the backscattered second light bundle 22' is deflected in the direction of the beam splitter 19 of the first measuring system 8. In a way similar to the beam splitter 13, in this configuration the beam splitter 19 is of frequency-selective design and to that extent transparent to the wavelength λ2, in order to ensure a quasi unattenuated transmission of the light bundle 22' onto the detector 48.

The Kepler telescope 17 disposed in accordance with FIG. 7 in the beam path of the second light bundle 22' fulfills the additional task of expanding the light bundle 22' in order to utilize the detection surface of the detector 48, and thus to exploit the resolution of the detector 48. The same goal is served by a further Kepler telescope 50 additionally disposed in accordance with FIG. 8 in the beam path of the second light bundle 22'.

In order to be able to separate from one another the signal components, detected by a common detector 48, of the two measuring systems 8 and 9, the measurements of topography and wave aberration are preferably carried out sequentially in time. The two measurements are performed in this case shortly after one another in such a way that the eye 2 remains quasi static during the entire measurement period. The measurements of topography and wave aberration are therefore performed quasi-simultaneously on the time scale of a typical reaction time of the eye 2. A simultaneous measurement of topography and wave aberration is, however, also possible with the aid of the common detector 48 to the extent that the latter includes a color-sensitive sensor, for example an RGB sensor. The signal components of the two measuring systems 8 and 9 can then be separated after the detection as a consequence of the different wavelength λ1 or λ2 of the two light bundles 11' and 22'.

We claim:

1. A device for measuring a topography and a wave aberration of a lens systems, the device comprising:
    a first measuring system having a first light source for emitting a first light bundle of a first wavelength, and a first detector for picking up the first light bundle reflected at the lens system;
    a second measuring system having a second light source for emitting a second light bundle of a second wavelength and a second detector for picking up the second light bundle transmitted through the lens system; and
    a diffractive optical element disposed in a common beam path region of said first and second measuring systems, said diffractive optical element adapting a respective wave-front profile of the first light bundle and of the second light bundle in a wavelength-selective fashion.

2. The device according to claim 1, wherein said diffractive optical element suppresses a zeroth diffraction order of the first light bundle, while the second light bundle is transmitted substantially undisturbed into the zeroth diffraction order.

3. The device according to claim 1, wherein said diffractive optical element preadapts the wave-front profile of the first light bundle to a topography of the lens system.

4. The device according to claim 1, wherein the wave-front profile of the second light bundle is substantially unmodified by said diffractive optical element.

5. The device according to claim 1, wherein said diffractive optical element is a surface-corrugated phase element.

6. The device according to claim 1, further comprising a third light source for emitting a third light bundle of a third wavelength for inserting a fixation target into the lens system.

7. The device according to claim 6, wherein the third wavelength corresponds to the second wavelength.

8. The device according to claim 1, wherein said first and second detectors are a common detector for said first and second measuring systems.

9. The device according to claim 1, wherein at least the first wavelength lies in the infrared spectral region.

10. The device according to claim 1, further comprising an adjusting configuration for setting a position of the lens system with reference to said diffractive optical element.

11. The device according to claim 10, wherein said adjusting configuration includes a light source for casting an adjusting light beam onto the lens system at an angle, and a position-sensitive detector for determining a position of the adjusting light beam reflected at the lens system.

12. The device according to claim 1, wherein said diffractive optical element is disposed directly upstream of the lens system.

13. The device according to claim 1, further comprising a wavelength-selective beam splitter limiting said common beam path region.

14. The device according to claim 13, wherein said wavelength-selective beam splitter is a diffractive optical element.

15. The device according to claim 1, wherein at least one of said first detector and said second detector is a Shack-Hartmann sensor.

16. The device according to claim 1, wherein at least one of said first detector and said second detector is an interferometer.

17. A method for measuring a topography and a wave aberration of a lens system, which comprises the steps of:
casting a first light bundle of a first wavelength onto the lens system for measuring the topography;
detecting the first light bundle reflected by the lens system;
casting a second light bundle of a second wavelength onto the lens system for measuring the wave aberration;
detecting the second light bundle transmitted through the lens system; and
adapting a respective wave-front profile of the first light bundle and of the second light bundle in a wavelength-selective fashion by a diffractive optical element positioned in a common beam path region of the first light bundle and of the second light bundle.

18. The method according to claim 17, which further comprises selecting the first wavelength and the second wavelength with regard to the diffractive optical element such that a zeroth diffraction order of the first light bundle is suppressed by the diffractive optical element, while the second light bundle is transmitted substantially unattenuated into the zeroth diffraction order.

19. The method according to claim 17, which further comprises preadapting the wave-front profile of the first light bundle to the topography of the lens system using the diffractive optical element.

20. The method according to claim 17, which further comprises measuring the topography and the wave aberration simultaneously.

21. The method according to claim 17, which further comprises measuring the topography and the wave aberration sequentially in time.

22. The method according to claim 17, which further comprises performing a scanning spot method for measuring the topography and/or the wave aberration.

* * * * *